(12) United States Patent
Jorgenson et al.

(10) Patent No.: US 7,221,457 B2
(45) Date of Patent: *May 22, 2007

(54) IMAGING PLATFORM FOR NANOPARTICLE DETECTION APPLIED TO SPR BIOMOLECULAR INTERACTION ANALYSIS

(75) Inventors: Ralph C. Jorgenson, Seattle, WA (US); David A. Basiji, Seattle, WA (US); William E. Ortyn, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/379,972

(22) Filed: Apr. 24, 2006

(65) Prior Publication Data

US 2006/0192955 A1    Aug. 31, 2006

Related U.S. Application Data

(63) Continuation of application No. 10/788,971, filed on Feb. 27, 2004, now Pat. No. 7,057,732, which is a continuation-in-part of application No. 10/628,662, filed on Jul. 28, 2003, now Pat. No. 6,975,400, which is a continuation-in-part of application No. 09/976,257, filed on Oct. 12, 2001, now Pat. No. 6,608,682, which is a continuation-in-part of application No. 09/820,434, filed on Mar. 29, 2001, now Pat. No. 6,473,176, which is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.

(60) Provisional application No. 60/451,346, filed on Feb. 27, 2003, provisional application No. 60/240,125, filed on Oct. 12, 2000, provisional application No. 60/117,203, filed on Jan. 25, 1999.

(51) Int. Cl.
*G01N 21/55* (2006.01)
(52) U.S. Cl. ...................................................... 356/445
(58) Field of Classification Search .................... None
See application file for complete search history.

(56) References Cited

U.S. PATENT DOCUMENTS 3,922,069 A    11/1975    Kishikawa et al. ......... 359/633

(Continued)

FOREIGN PATENT DOCUMENTS

WO    WO 00/42412    7/2000

OTHER PUBLICATIONS

Kubota, Fumio et al. 1995. "Flow Cytometer and Imaging Device Used in Combination." *Cytometry:* 21:129-132.

(Continued)

*Primary Examiner*—Michael P. Stafira
(74) *Attorney, Agent, or Firm*—Ronald M. Anderson

(57) ABSTRACT

A flow imaging system is used to implement surface plasmon resonance (SPR) detection to study bio-molecular interactions. The flow imaging system is used to capture SPR absorption spectra of large numbers of objects, where each object includes both a metal film capable of exhibiting SPR, and detecting molecules. Analyte molecules are added to a solution of such objects, and the result is introduced into the flow imaging system which collects full SPR spectral data from individual objects. The objects can be nanoparticles or larger particles that support metal island films. The SPR spectral data can be used to determine specificity, kinetics, affinity, and concentration with respect to the interactions between the detecting molecules and the analyte molecules.

16 Claims, 9 Drawing Sheets

U.S. PATENT DOCUMENTS

| | | | | |
|---|---|---|---|---|
| 4,635,293 | A | 1/1987 | Wantanabe | 382/130 |
| 4,677,680 | A | 6/1987 | Harima et al. | 382/112 |
| 4,770,992 | A | 9/1988 | Van den Engh et al. | 435/6 |
| 4,786,165 | A | 11/1988 | Yamamoto et al. | 356/23 |
| 5,096,807 | A | 3/1992 | Leaback | 435/6 |
| 5,141,609 | A | 8/1992 | Sweedler et al. | 356/344 |
| 5,153,916 | A | 10/1992 | Inagaki et al. | 382/151 |
| 5,159,397 | A | 10/1992 | Kosaka et al. | 356/73 |
| 5,159,398 | A | 10/1992 | Maekawa et al. | 356/73 |
| 5,159,642 | A | 10/1992 | Kosaka | 382/6 |
| 5,247,339 | A | 9/1993 | Ogino | 356/73 |
| 5,272,354 | A | 12/1993 | Kosaka | 250/574 |
| 5,351,311 | A | 9/1994 | Rogers | 382/156 |
| 5,422,712 | A | 6/1995 | Ogino | 356/73 |
| 5,444,527 | A | 8/1995 | Kosaka | 356/73 |
| 5,471,294 | A | 11/1995 | Ogino | 356/73 |
| 5,548,395 | A | 8/1996 | Kosaka | 356/73 |
| 5,596,401 | A | 1/1997 | Kusuzawa | 356/23 |
| 5,633,503 | A | 5/1997 | Kosaka | 250/458.1 |
| 5,644,388 | A | 7/1997 | Maekawa et al. | 356/73 |
| 5,674,743 | A | 10/1997 | Ulmer | 435/287.2 |
| 5,695,934 | A | 12/1997 | Brenner | 435/6 |
| 5,754,291 | A | 5/1998 | Kain | 356/344 |
| 5,760,899 | A | 6/1998 | Eismann | 356/326 |
| RE35,868 | E | 8/1998 | Kosaka | 250/574 |
| 5,831,723 | A | 11/1998 | Kubota et al. | 356/73 |
| 5,848,123 | A | 12/1998 | Strommer | 378/98.8 |
| 5,855,753 | A | 1/1999 | Trau et al. | 204/484 |
| 5,929,986 | A | 7/1999 | Slater et al. | 356/326 |
| 5,959,953 | A | 9/1999 | Alon | 369/44.41 |
| 6,007,994 | A | 12/1999 | Ward et al. | 435/6 |
| 6,014,468 | A | 1/2000 | McCarthy et al. | 382/254 |
| 6,066,459 | A | 5/2000 | Garini et al. | 435/6 |
| 6,116,739 | A | 9/2000 | Ishihara et al. | 353/31 |
| 6,156,465 | A | 12/2000 | Cao et al. | 430/30 |
| 6,210,973 | B1 | 4/2001 | Pettit | 436/172 |
| 6,211,955 | B1 | 4/2001 | Basiji et al. | 356/326 |
| 6,249,341 | B1 | 6/2001 | Basiji et al. | 356/73 |
| 6,256,096 | B1 | 7/2001 | Johnson | 356/335 |
| 6,330,081 | B1 | 12/2001 | Scholten | 358/463 |
| 6,330,361 | B1 | 12/2001 | Mitchell et al. | 382/211 |
| 6,381,363 | B1 | 4/2002 | Murching et al. | 382/164 |
| 6,522,781 | B1 | 2/2003 | Norikane et al. | 382/203 |
| 6,549,664 | B1 | 4/2003 | Daiber et al. | 382/232 |
| 6,763,149 | B2 | 7/2004 | Riley et al. | 382/294 |
| 7,006,710 | B2 | 2/2006 | Riley et al. | 382/294 |
| 7,057,732 | B2* | 6/2006 | Jorgenson et al. | 356/445 |
| 2001/0006416 | A1 | 7/2001 | Johnson | 356/73 |
| 2002/0126275 | A1 | 9/2002 | Johnson | 356/317 |

OTHER PUBLICATIONS

Kubota, F. 2003. "Analysis of red cell and platelet morphology using an imaging-combined flow cytometer." *Clin. Lab. Haem.:* 25:71-76.

Ong, Sim Heng. 1985. Development of a System for Imaging and Classifying Biological Cells in a Flow Cytometer. Doctor of Philosophy Thesis. University of Sydney, School of Electrical Engineering. (August).

Ong, S.H. et al. 1987. "Development of an Image Flow Cytometer." *Analytical and Quantitative Cytology and Histology. XIVth International Conference on Medical and Biological Engineering and VIIth International Conference on Medical Physics*, Finland. (August): 375-382.

Ong, S.H. and P.M. Nickolls. 1991. "Optical Design in a Flow System For Imaging Cells." *Sciences in Medicine:* 14:2:74-80.

Ong, S.H. and P.M. Nickolls. 1994. "Analysis of MTF Degradation in the Imaging of Cells in a Flow System." *International Journal of Imaging Systems & Technology:* 5:243-250.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry:* 48:194-201.

Wang, Fu-sheng and Fumio Kubota. 2002. "A Novel Apoptosis Research Method With Imaging-Combined Flow Cytometer and HITC OR IR-125 Staining." *Cytometry:* 50:267-274.

Wietzorrek, Joachim et al. 1999. "A New Multiparameter Flow Cytometer: Optical and Electrical Cell Analysis in Combination With Video Microscopy in Flow." *Cytometry:* 35:291-301.

\* cited by examiner

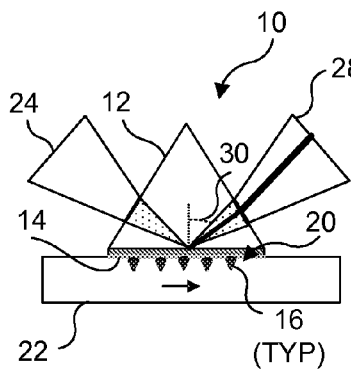
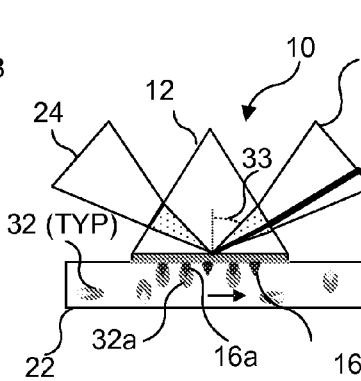
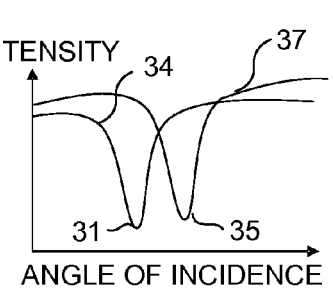
FIG. 1A PRIOR ART  FIG. 1B PRIOR ART  FIG. 1C PRIOR ART
FIG. 1D/PRIOR ART
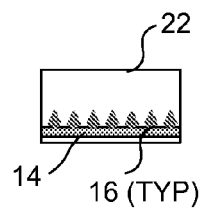
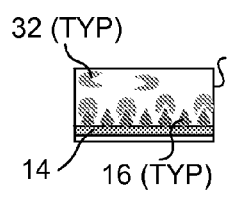
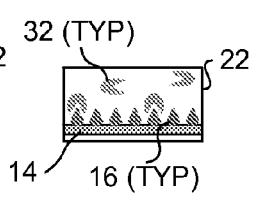
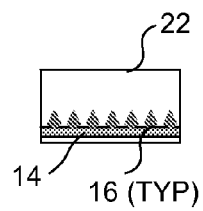
FIG. 1E  FIG. 1F  FIG. 1G  FIG. 1H
PRIOR ART

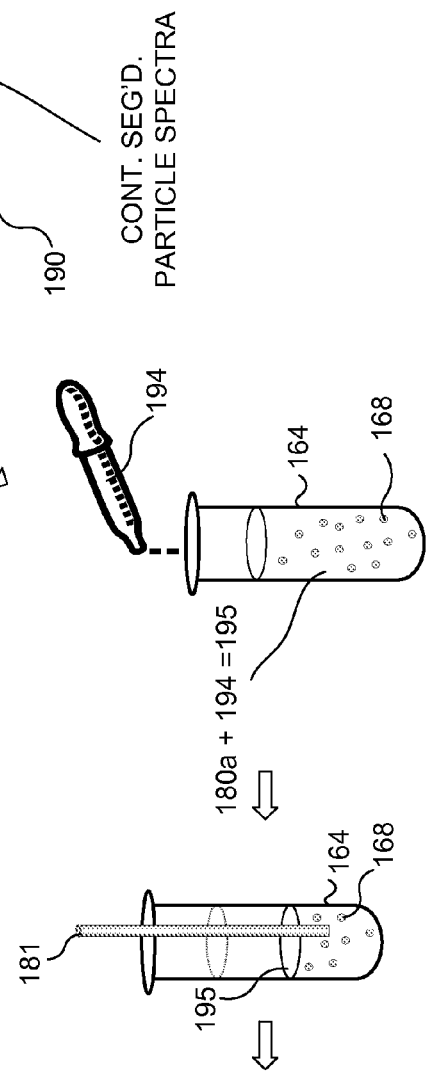
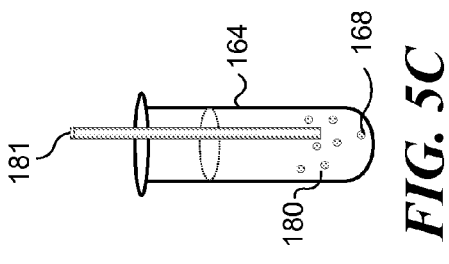
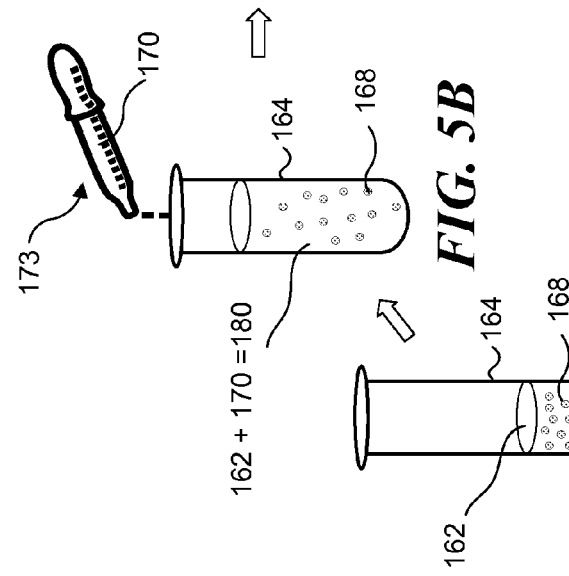
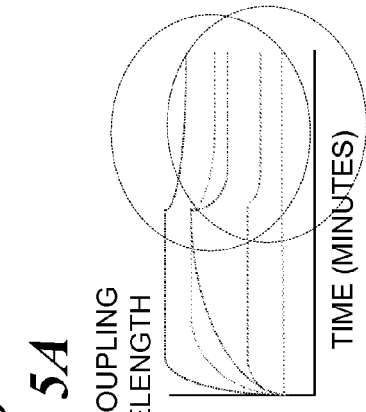

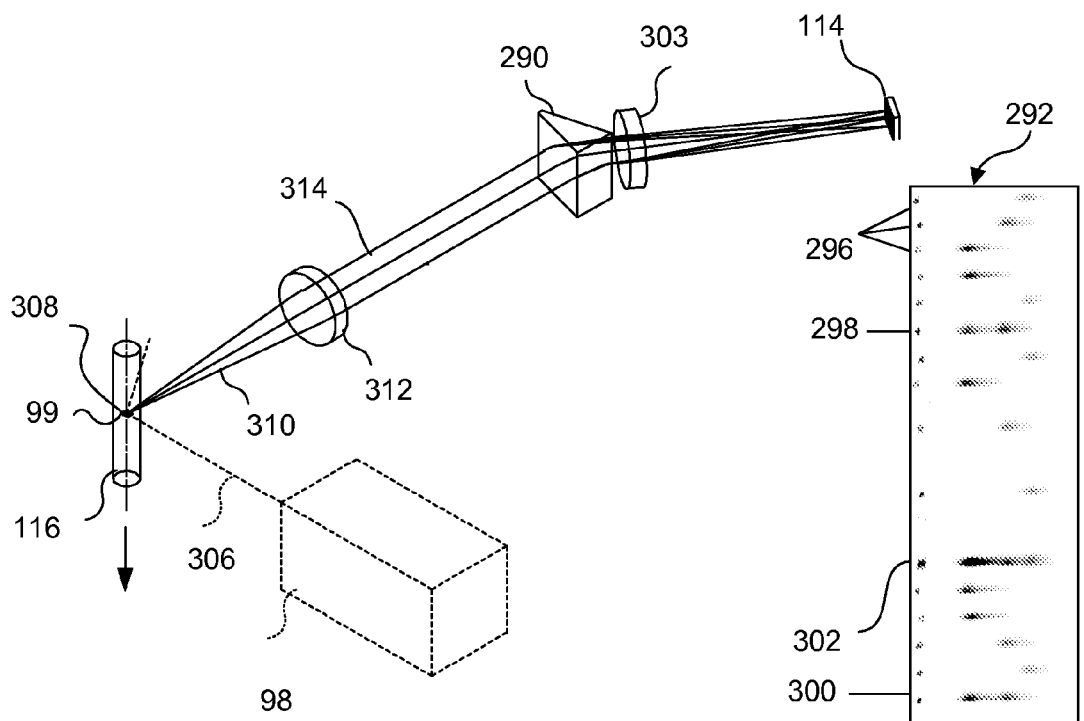
FIG. 8A
FIG. 8B
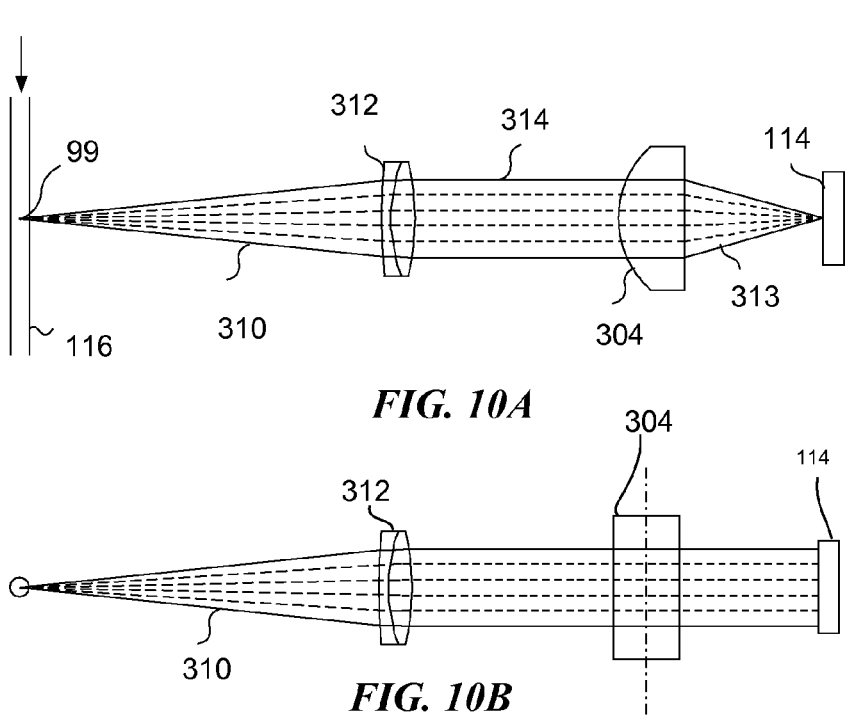
FIG. 10A
FIG. 10B

IMAGING PLATFORM FOR NANOPARTICLE DETECTION APPLIED TO SPR BIOMOLECULAR INTERACTION ANALYSIS

RELATED APPLICATIONS

This application is a continuation application based on a prior copending conventional application Ser. No. 10/788,971, filed on Feb. 27, 2004, now U.S. Pat. No. 7,057,732 which itself is based on provisional application Ser. No. 60/451,346, filed on Feb. 27, 2003, and which is also a continuation-in-part of patent application Ser. No. 10/628,662, filed on Jul. 28, 2003, which issued as U.S. Pat. No. 6,975,400 on Dec. 13, 2005, which itself is a continuation-in-part application of patent application Ser. No. 09/976,257, filed on Oct. 12, 2001, which issued as U.S. Pat. No. 6,608,682 on Aug. 19, 2003, which itself is a continuation-in-part application of patent application Ser. No. 09/820,434, filed on Mar. 29, 2001, which issued as U.S. Pat. No. 6,473,176 on Oct. 29, 2002, which itself is a continuation-in-part application of patent application Ser. No. 09/538,604, filed on Mar. 29, 2000, which issued as U.S. Pat. No. 6,211,955 on Apr. 3, 2001, which itself is a continuation-in-part application of patent application Ser. No. 09/490,478, filed on Jan. 24, 2000, which issued as U.S. Pat. No. 6,249,341 on Jun. 19, 2001, which itself is based on provisional patent application Ser. No. 60/117,203, filed on Jan. 25, 1999, the benefit of the filing dates of which is hereby claimed under 35 U.S.C. §120 and 35 U.S.C. §119(e). patent application Ser. No. 09/976,257, noted above, is also based on provisional application Ser. No. 60/240,125, filed on Oct. 12, 2000, the benefit of the filing date of which is hereby claimed under 35 U.S.C. §119(e).

BACKGROUND OF THE INVENTION

SPR is the resonant excitation of oscillating free charges at the interface of a metal and a dielectric. When SPR spectra are generated and collected, they can be used to determine specificity, kinetics, affinity, and concentration with respect to the interactions between two or more molecules, where one of the molecules is attached to a solid sensing surface. Reaction kinetics correspond to both an association and a dissociation rate at which an analyte interacts with the bound detection molecule. Affinity refers to the strength with which an analyte binds to the detecting molecule. Specificity refers to the propensity of a molecule to bind to the detecting molecule to the exclusion of other molecules. SPR spectra have been used in studies involving many types of molecules including proteins, peptides, nucleic acids, carbohydrates, lipids, and low molecular weight substances (e.g., hormones and pharmaceuticals).

One analytical technique, known as SPR based bio-sensing, has been developed to enable direct measurements of the association of ligands with receptors, without the use of indirect labels, such as fluorescent markers and radioactive molecular tags. This label free direct sensing technique reduces the time and workload required to perform assays, and minimizes the risk of producing misleading results caused by molecular changes induced by the use of indirect labels. Another important aspect of the bio-sensing technique is that SPR based bio-sensing enables bio-molecular interactions to be measured continuously and in real-time, thereby enabling the determination of association and dissociation kinetic data in contrast to traditional "end point" analytical methods.

The utility and acceptance of SPR based bio-sensing is evident from the over 2,500 peer-reviewed scientific papers that have been published, which cite the use of SPR technology. To date, there is an estimated installed base of 1,500 research grade SPR analytical instruments in basic and applied research laboratories at universities, national research centers, and major pharmaceutical and biotechnology companies around the world. The diversity of recently published articles relating to bio-molecular interaction analysis include such applications as drug discovery (lead identification and target validation), ligand fishing, comparative binding specificity, mutation studies, cell signaling, multi-molecular complexes, immune regulation, immunoassays, vaccine development, and chromatographic development. Such SPR based research tools are of great value to researchers involved in basic and applied life sciences who are studying the function of molecules in biological systems.

Over the past decade, interest in the unique optical properties of metallic and semiconductor nanoparticles has increased considerably with respect to the use of suspensions and films incorporating these nanoparticles for the purposes of exciting surface plasmons to enable the detection of SPR spectra. In addition, surface enhanced Raman spectroscopy can be used to obtain infrared absorbance spectral information, and surface enhanced fluorescence for enhanced fluorescence stimulation. Nanoparticles are particles that are less than 100 nanometers in diameter. They display large absorbance bands in the visible wavelength spectrum yielding colorful colloidal suspensions. The physical origin of the light absorbance is due to incident light energy coupling to a coherent oscillation of the conduction band electrons on the metallic nanoparticle. This coupling of incident light is unique to discrete nanoparticles and films formed of nanoparticles (referred to as metallic island films). Achieving SPR with ordinary bulk materials requires the use of a prism, grating, or optical fiber to increase the horizontal component of the incident light wave vector (i.e., to achieve the required coupling).

Historically, gold nanoparticles have been used as a pigment in stained glass as early as 350 years ago. Chemist and physicist Michael Faraday first recognized that the color of this stained glass was a result of the metallic gold being in a colloidal form, and Gustaf Mie explained this phenomenon theoretically in 1908, by solving Maxwell's equation for absorption and scattering of electromagnetic radiation by a spherical particle.

Recently, sensor devices have been developed in the known art to exploit the unique optical properties of these nanoparticles. SPR measurements have been made using gold nanoparticle suspensions to detect biomolecular interactions in real time by monitoring the absorbance of colloidal suspensions. Similarly, SPR has been excited using polystyrene and silica beads with silver and gold island films and hollow gold nanoshells. However, to date, all such measurements have been performed primarily on bulk homogeneous suspensions of nanoparticles, due to the challenge of individually addressing and detecting these small objects.

For example, FIGS. 1A and 1B schematically illustrate a simplified version of a prior art SPR detection device including a single channel SPR bulk optic prism based sensor 10, which includes a prism 12. The base of prism 12 is covered with a layer 14 of gold about 550 Ångstroms thick. The gold film is pre-functionalized with a defined detecting molecule 16, such as an antigen. A biological fluid sample containing a corresponding analyte 32 (such as an antibody) is brought into contact with gold layer 14 and detecting molecules 16 by introducing the sample fluid into a flow cell 22 (note gold layer 14 and detecting molecules 16 together represent a sensor surface 20, which is in fluid communication with flow cell 22). A range of angles of monochromatic light 24 are directed towards and reflected from sensor surface 20. SPR arises through the coupling of energy between the incident photons of light with free electron oscillations ("plasmons") occurring at a gold film/liquid chemical sample interface at sensor surface 20. This interaction can cause a reduction in an intensity of reflected light 28 for a given angle 30, resulting in an absorbance or "resonance" dip 31 in a measured reflectance spectrum 34 (see FIG. 1C). This resonance can also be observed in the wavelength domain if white light is introduced at an optimal fixed angle of incidence. When an analyte 32 binds to immobilized detecting molecule 16 on sensor surface 20 (see analyte 32a and molecule 16a of FIG. 1B), the local mass concentration of molecules changes, which causes a corresponding change in the local refractive index close to sensor surface 20. The resultant increase in the refractive index causes a shift in the resonance angle, from angle 30 as illustrated in FIG. 1A, to an angle 33 in FIG. 1B. Angle 33 results in a "resonance" dip 35 in a measured reflectance spectrum 37, which is readily distinguishable from spectrum 34 (no binding event, so the reflectance angle is unchanged). Sensor 10 enables data collection to be performed continuously and in real-time, and some systems enable the user to observe the binding events in real time on a personal computer.

This bio-sensing technique was first reported in 1983, and first commercialized in 1990. Since then many different optical geometries have been explored including: (i) the Otto configuration, which utilizes an air gap between the optical coupling prism and the SPR supporting metal; (ii) the Kretschmann configuration, which eliminates the need for an air gap in favor of the metal film directly deposited upon the prism base; (iii) the use of a diffraction grating to excite SPR; (iv) an optical fiber configuration, wherein metal is deposited cylindrically around the fiber core; (v) planar/channel waveguide configurations with retro-reflective elements; (vi) microstructure systems that have an integrated light source, detector, and guiding optics, including a capillary configuration in which SPR is excited in the interior capillary walls; (vi) use of gold island films; and (vii) two-dimensional (2D) imaging techniques for SPR array-based sensing.

FIG. 1D graphically illustrates a typical SPR response curve 38 based on the association and dissociation of two bio-molecules. Curve 38 can be separated into four well-defined segments, each relating to a specific portion of an association/disassociation cycle. The portion of the cycle corresponding to segment A is schematically illustrated in FIG. 1E. Flow cell 22 is in fluid communication with detecting molecules 16, which are bound to gold layer 14. While no prism is shown in conjunction with FIGS. 1E–1H, it should be understood that the flow cells of FIGS. 1E–1H are used in with a prism, as shown in sensor 10 of FIGS. 1A and 1B.

Referring once again to FIG. 1E, since analyte molecules are currently not present in flow cell 22, there is no change in the angle of incidence in section A of spectrum 38 (FIG. 1D). Generally the flow cell is filled with a buffer solution during this time period. Portion A of spectrum 38 is thus referred to as a baseline response.

In FIG. 1F (corresponding to portion B of spectrum 38), molecules of analyte 32 are introduced into flow cell 22 (i.e., a sample fluid containing the analyte is introduced into the flow cell). Some of the molecules of analyte 32 bind to detecting molecules 16, and the angle of incidence changes over time. Response curve 38 of FIG. 1D typically represents a time period of about 5 to 20 minutes in duration. This response level indicates the baseline response. During this "association" period, the analyte binds to the surface, thereby increasing the refractive index, causing the SPR resonant angle to increase (note the rise in portion B of spectrum 38).

In FIG. 1G (corresponding to portion C of response curve 38), no additional analyte is introduced into the flow cell. Instead, the flow cell is flushed with a buffer solution. This step results in analytes being released from detection molecules 16, as the bound analytes 32 attempt to reach an equilibrium with the buffer solution. The decrease in the amount of bound analyte is reflected in a dip in spectrum 38.

In FIG. 1G (corresponding to portion D of spectrum 38), the flow cell is flushed with an acidic solution, which ensures that any residual bound analytes are removed from the detection molecules, thereby regenerating the sensor surface. This "regeneration" step enables the sensor surface to be returned to its original baseline configuration, so that further analyses can be performed. As noted above, the data collected during portions A–D of spectrum 38 (often referred to as a Sensorgram) enable the user to determine kinetics, concentration, binding specificity, and affinity.

FIG. 2 shows a different prior art technique that has been developed, which also involves exciting and detecting SPR on gold and silver nanoparticles. Chemical and biological sensing applications using nanoparticles have been performed primarily by measuring a transmitted light intensity 80 through a high concentration of suspended particles 82. The resultant spectrum 84 has an absorbance dip 86 due to the excitation of SPR at a certain coupling wavelength 88, as shown in FIG. 2. The exact position and shape of the SPR spectrum is a function of such factors as the metal used, the bulk solution and adsorbed film complex refractive indices, the adsorbed film thickness, the nanoparticle morphology (size and shape), and inter-particle coupling effects (e.g. the concentration and proximity of nanoparticles to one another). For small nanoparticles compared to the wavelength, $\lambda$, the extinction cross section for the nanoparticles, can be approximated as indicated in Eq. 1, as follows:

$$\sigma_{ext} \approx \frac{9V\varepsilon_b^{3/2}}{c} \cdot \frac{\omega\varepsilon_2(\omega)}{[\varepsilon_1(\omega) + 2\varepsilon_b]^2 + \varepsilon_2(\omega_2)^2} \quad (1)$$

where V is the spherical nanoparticle volume, c is the speed of light, $\omega$ is the angular frequency of the incident light, $\varepsilon_b$ is the permittivity of the surrounding bulk dielectric medium (assumed to be relatively independent of the frequency of light), $\varepsilon_1(\omega)$ and $\varepsilon_2(\omega)$ denote the real and imaginary parts of the metal permittivity, or more specifically, $(\varepsilon(\omega)) = \varepsilon_1(\omega) + i\varepsilon_2(\omega)$).

For nanoparticle SPR measurements, the maximum absorbance wavelength, $\lambda_{spr}$ (SPR coupling wavelength) dependence on refractive index is not as sensitive as the bulk thin film SPR measurements. Sensitivity of a 75 nanometer shift in the SPR coupling wavelength per refractive index unit (RIU) is reported, as compared to 3000 nanometer shift per RIU for bulk film SPR devices. Thus, gold nanoparticle SPR measurement based methods are 40 times less sensitive. However, additional geometries, including gold/silver alloy nanoparticles, ellipsoidal nanoparticles, triangular nanoparticles, and hollow nanoshells have been reported as having increased sensitivities up to six fold (400 nm wavelength shift per RIU).

Although bulk SPR devices exhibit increased sensitivity to refractive index over SPR nanoparticle devices, the nanoparticles have an advantage with respect to the sensitivity of adsorption of molecules to the gold surface. Specifically, the decay length of the electric field extending from the gold/chemical sample interface is approximately 20 times shorter for that of nanoparticle colloidal gold versus bulk thin gold film. Therefore, because nanoparticles have more energy confined closer to the gold surface, these particles are more surface sensitive and will yield a larger signal during receptor/ligand interactions.

However, the above mentioned prior art techniques are currently limited by throughput, mass transport diffusion, and depletion of small concentrations of analytes. Commercial SPR biosensors are currently limited to four-channel detection. This fact, and the relatively high degree of training necessary to operate these instruments and analyze the results, currently limit SPR analytical use in the laboratory. In contrast, other bio-molecular analytical methods, such as immunological assays, and spectroscopic techniques (absorption, fluorescence spectroscopy, and fluorescent polarization) have kept up with increased analytical demands by making available instruments having, for example, 96, 384, and 1,536 micro-wells. It should be noted that there are several publications directed towards multi-spot or 2D array SPR sensors. However, most if not all of these approaches are directed toward optical configurations that can only detect a single angle or single wavelength intensity. Therefore, changes in the association or dissociation of bio-molecules are detected as an intensity change, which has limited sensitivity and limited dynamic range compared to full spectral SPR data, where the entire angular or wavelength spectrum is measured, enabling a high precision measurement of the coupling angle or wavelength.

Current commercial SPR instrumentation uses a fixed sensor having a gold layer capable of supporting SPR, such as the traditional SPR bulk optic prism based sensor shown in FIGS. 1A and 1B. The bio-molecular receptor molecules attached to the gold layer are analyte specific. The analyte is brought to this sensor surface via fluidics, and the analyte associates with the bound receptor molecules on the sensor surface. Current planar embodiments are severely mass transport limited by diffusion to time scales on the order of 16 to 160 minutes for analytes at bulk concentrations less than $10^{-7}$ M.

Finally, current commercial SPR instrumentation uses sensors that have relatively large areas (e.g., four, twelve, and a hundred square millimeters). Because the SPR signal is proportional to the density of binding, having a large sensor area limits the analyte sensitivity, since low concentration analyte binding serves to deplete the analyte concentration near the surface.

It would therefore be desirable to provide apparatus and a method that address and detect individual nanoparticles and particles, enabling high throughput and full spectrum SPR measurement, measuring the association of molecules free in solution via SPR emitted from nanoparticles and micro particles suspended in solution, employing a significantly reduced sensor area with improved analyte sensitivity, providing a label-free direct sensing approach that reduces time and workload needed to carryout assays, and measuring biomolecular interactions continuously and in real-time. The prior art does not teach or suggest a complete solution to the problems discussed above.

SUMMARY OF THE INVENTION

A first aspect of the invention is directed to an SPR biomolecular interaction method that uses flow imaging systems, which can combine the speed, sample handling, and cell sorting capabilities of flow cytometry with the imagery, sensitivity, and resolution of multiple forms of microscopy and full visible/near infrared spectral analysis of detector technology to collect and analyze SPR spectra from objects entrained in a flow of fluid that emit an SPR spectra. This method includes the steps of placing gold or silver nanoparticles or beads that have a detector molecule attached to them in a container, adding a solution of analyte or ligand molecules to the container, and introducing a portion of the sample into a flow imaging system. The flow imaging system provides up to a thousand-fold increase in signal collection over conventional SPR instrument designs and allows for maintaining particles in suspension to ensure optimal free solution conditions for association and dissociation of bio-molecular species. This approach is thus not severely mass transport limited, like planar embodiments. A peak absorbance wavelength can then be measured using detector technology. Since full spectral SPR data can be collected with this detector technology, the entire angular or wavelength spectrum is measured, providing a very precise measurement of the coupling angle or wavelength. In addition, this approach has the ability to measure libraries of different bead receptors. Also, this method includes repeating these steps on the portion of the sample that remains in the container. After centrifuging, removing the supernatant, and adding a buffer solution, this buffered portion of the remaining sample can be introduced into the flow imaging system, and disassociation rates can be studied. If desired, an optional step can be employed, wherein a low pH wash is used to remove the bound ligands from the receptors attached to the nanoparticles, and repeated measurements can then be made.

Corrections can be made to a nanoparticle response curve that exhibits a non-linear response. Specifically, larger nanoparticles may be used to increase the curve's linearity, and calibration corrections can be made for the non-linear response.

The preferred flow imaging systems can be used to analyze white light spectral scatter analysis of gold nanoparticles and nanoparticle-coated microbeads using prism dispersion. A prism or grating is employed to disperse laterally high resolution white light spectral scatter spectra of the nano or micro particles being analyzed.

Yet another step of this method involves collecting simultaneous imaging of absorbed, scattered, and fluorescent light from microbeads.

Furthermore, if the prism is removed from the preferred flow imaging system and a focusing spherical lens is replaced with a cylindrical lens, the high resolution scattered angular spatial intensity of the nano or micro particle can be measured under monochromatic side illumination.

Another aspect of this invention provides for multispectral darkfield scattering to analyze particles. For particles with sizes equal or smaller than the pixel size in the image plane, the size of such particle can be determined by measuring the relative light scattering intensity across multiple wavelengths. The ratio of the scattered light intensities at given wavelengths is a function of the size of the particle, based upon Raleigh scattering.

Furthermore, a holographic notch filter can be used with the preferred imaging system to filter out the excitation laser light signal to enable surface enhanced Raman spectroscopy.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1A schematically illustrates a prior art SPR sensor including a thin layer of gold and a prism;

FIG. 1B schematically illustrates analytes being attracted to specific detection molecules attached to the gold film in the prior art SPR sensor of FIG. 1A;

FIG. 1C is a graph illustrating the relationship between an intensity of light reflected from the gold layer through the prism and an angle of incidence with which such light is reflected using the prior art SPR sensor of FIG. 1A;

FIG. 1D is a graph illustrating a characteristic relationship between a resonant angle and time based on a preferred analytical technique using the prior art SPR sensor of FIG. 1A;

Figure 2:
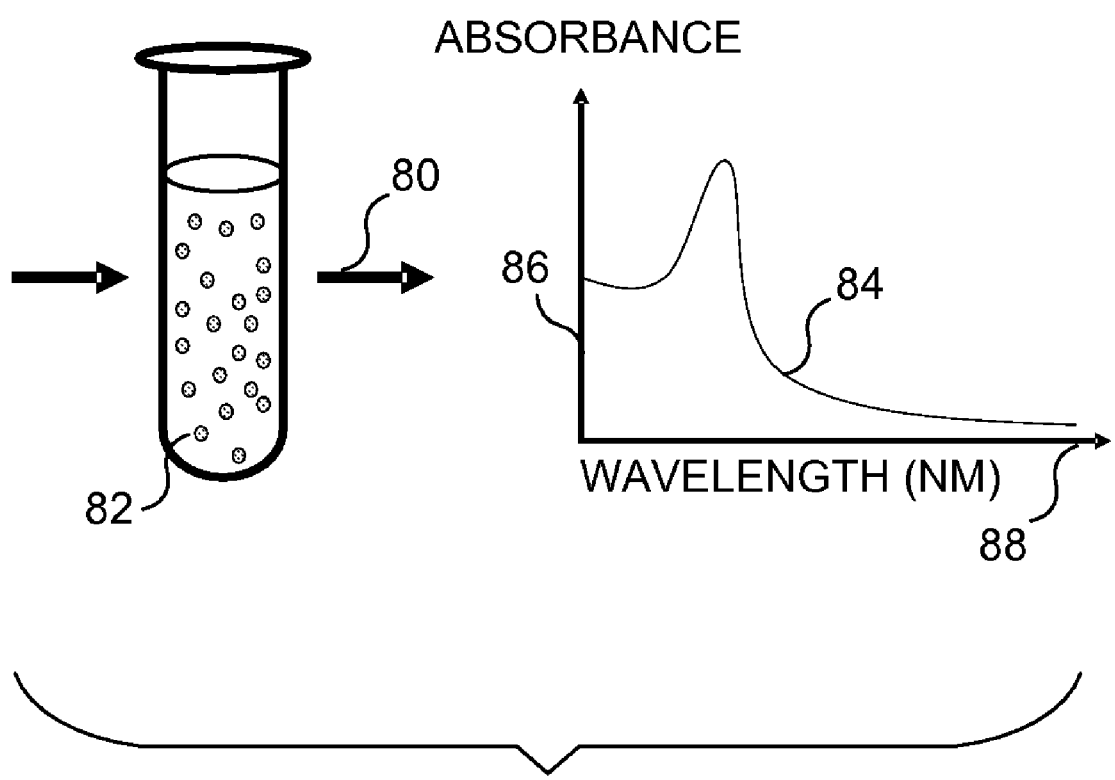
Figure 3:
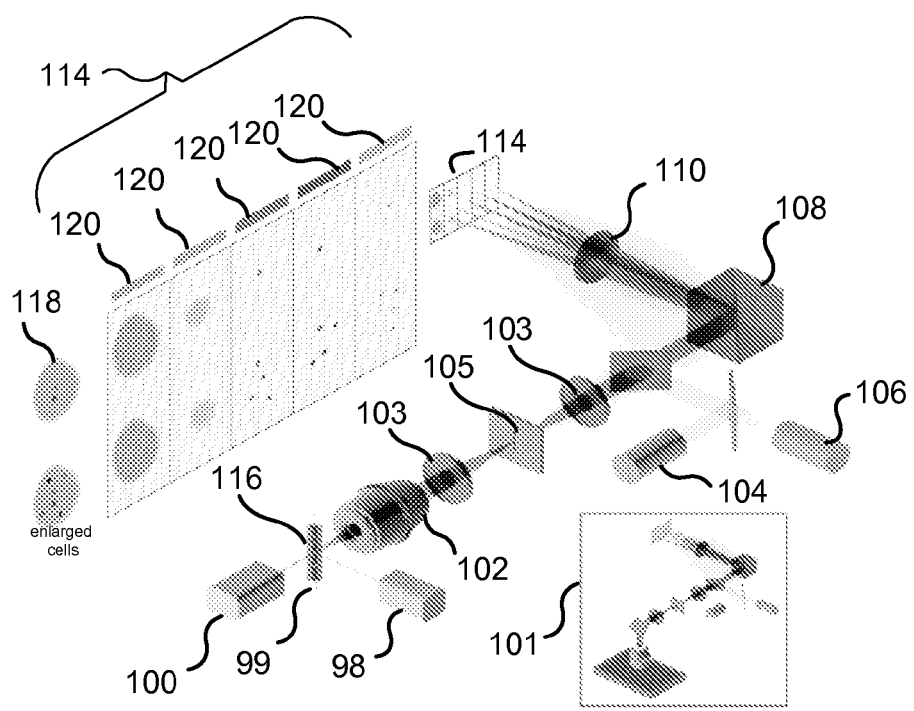
Figure 4:
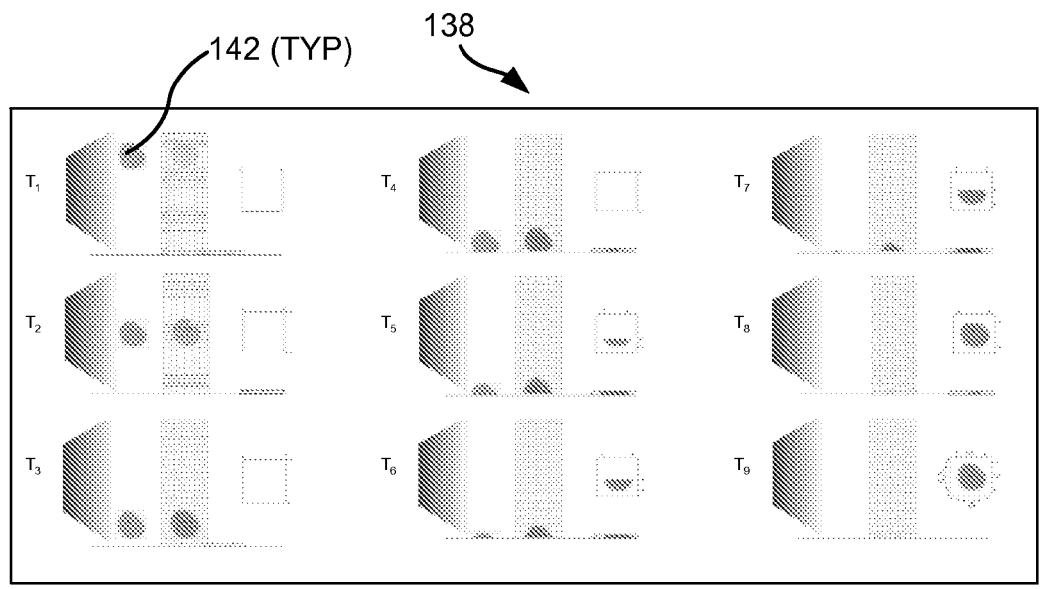
Figure 6:
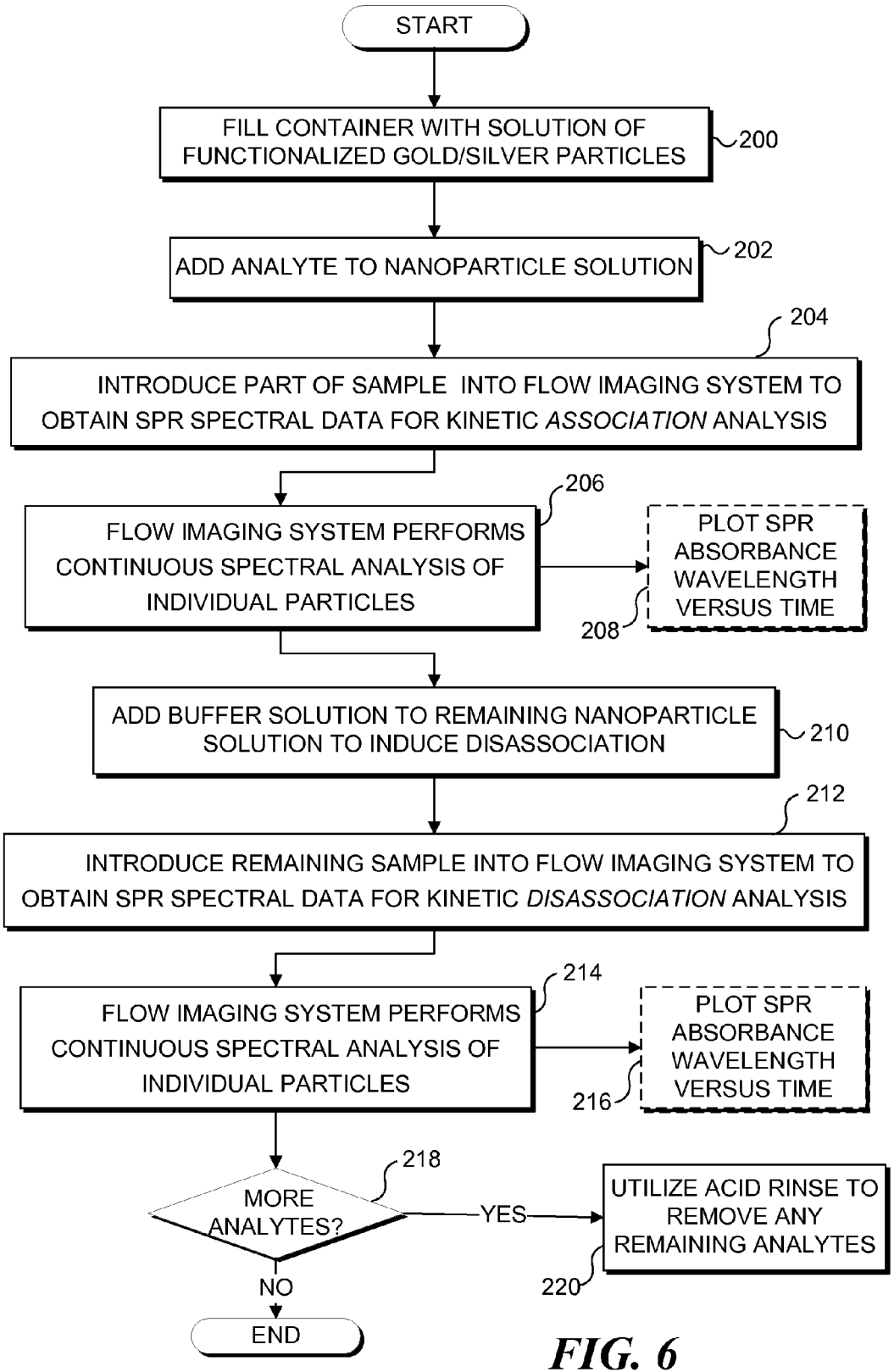
Figure 7:
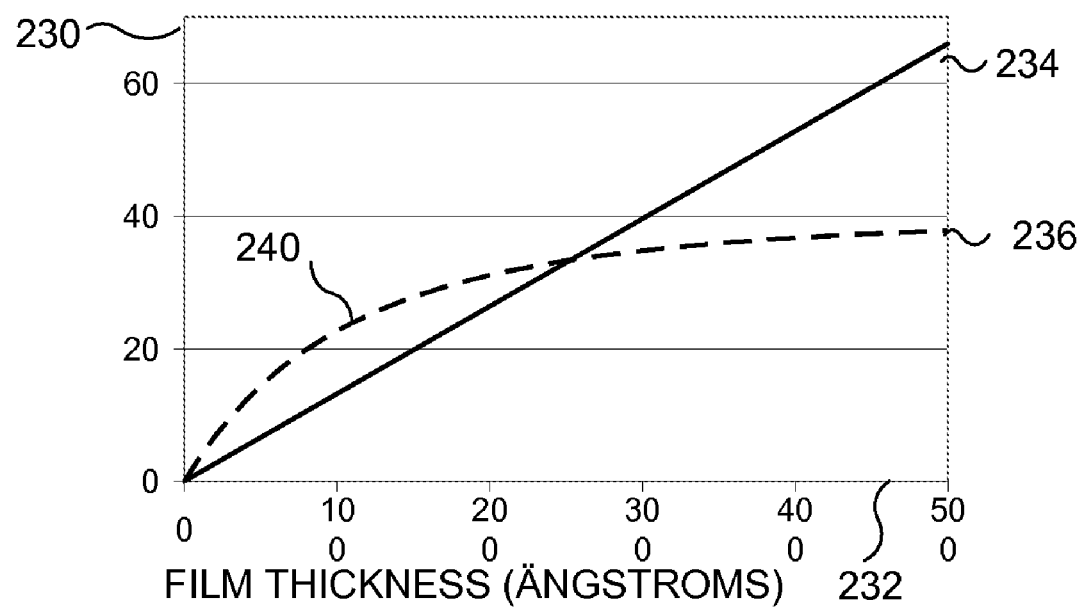
Figure 9:
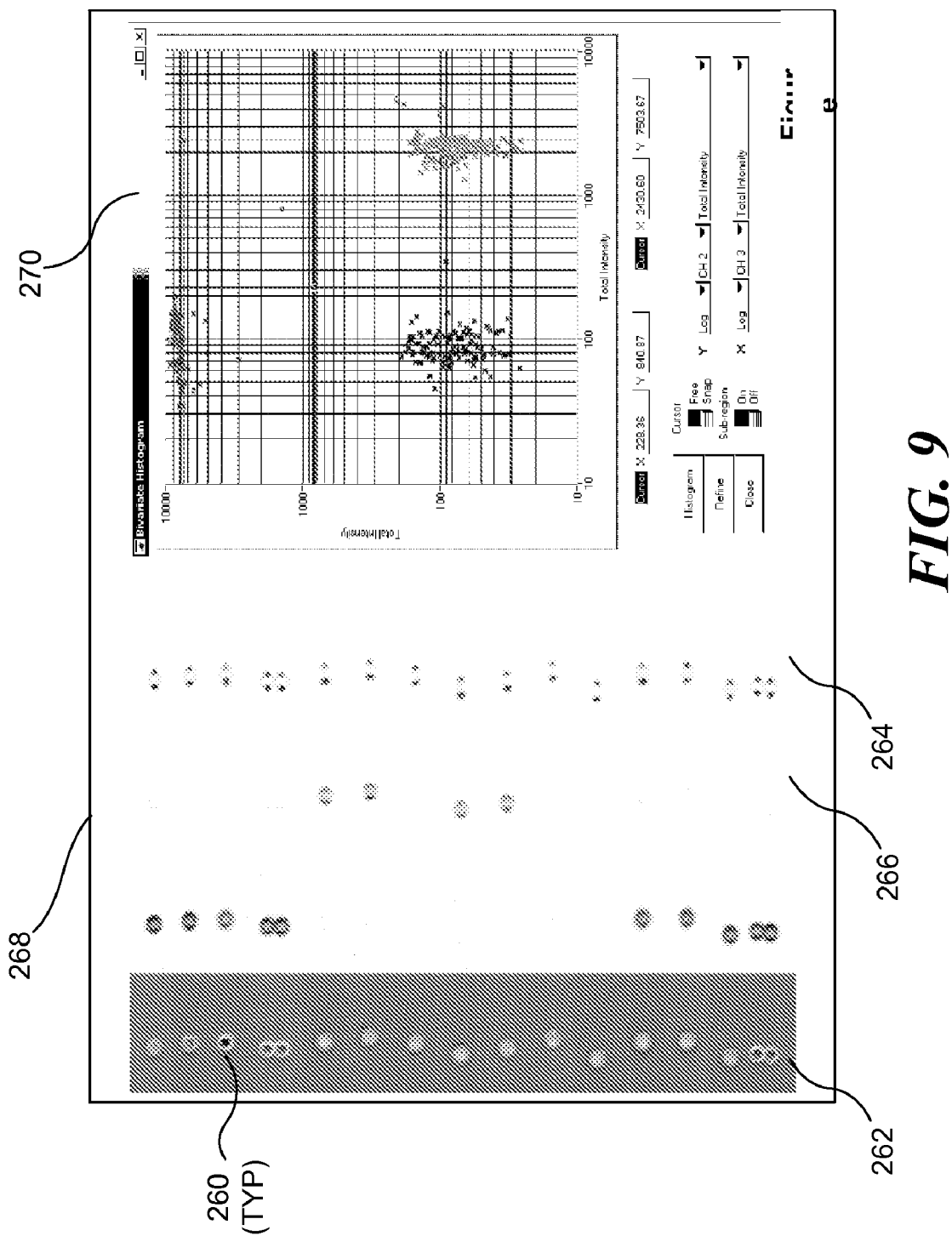
Figure 11:
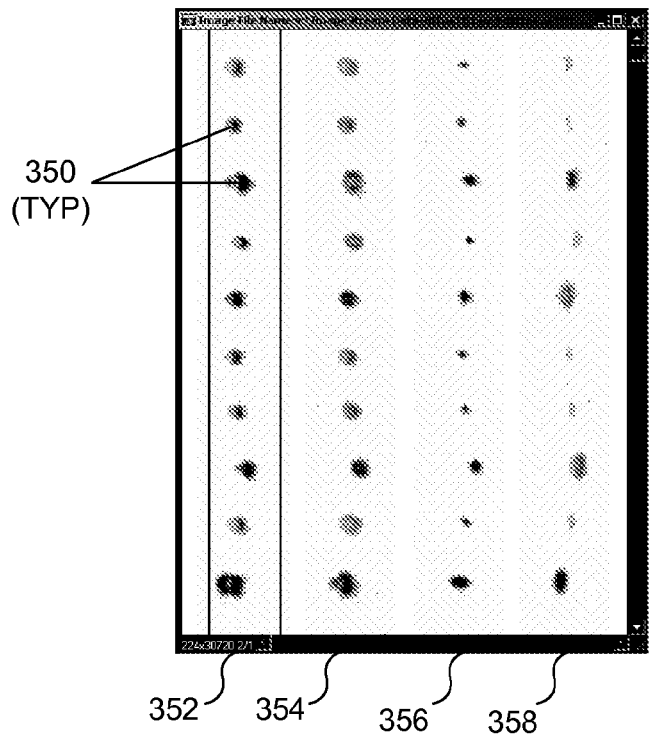
Figure 12:
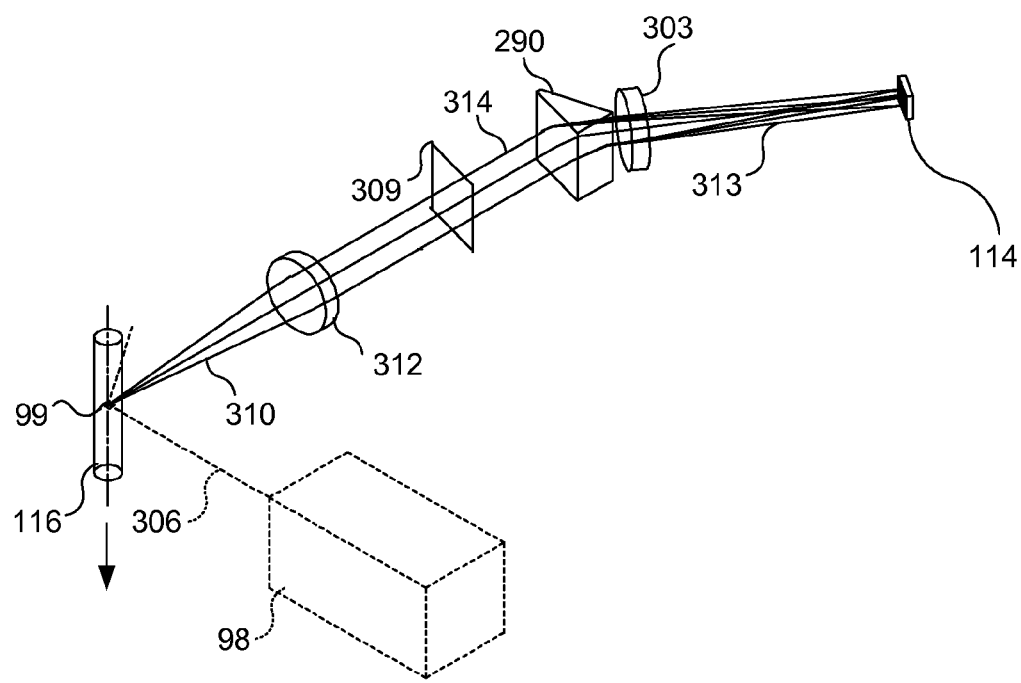

FIG. 1E schematically illustrates a first step in a preferred prior art technique for using the prior art SPR sensor of FIG. 1A;

FIG. 1F schematically illustrates a second step in a preferred prior art technique for using the prior art SPR sensor of FIG. 1A;

FIG. 1G schematically illustrates a third step in a preferred prior art technique for using the prior art SPR sensor of FIG. 1A;

FIG. 1H schematically illustrates a fourth step in a preferred prior art technique for using the prior art SPR sensor of FIG. 1A;

FIG. 2 schematically illustrates a prior art technique for obtaining a transmission measurement from a bulk solution of gold nanoparticles;

FIG. 3 is a schematic illustration of a preferred flow imaging system used in accord with the present invention;

FIG. 4 is a schematic illustration of a readout provided by a time delay integrated (TDI) detector employed in a preferred imaging system used in accord with the present invention;

FIGS. 5A–5G schematically illustrate a method for using the flow imaging system of FIG. 3 and the detector technology of FIG. 4 for bio-molecular interaction analysis, in connection with nanoparticle or micro particle SPR substrates;

FIG. 6 is a flow chart showing the steps of the method illustrated in FIG. 5A–5G, including an additional step for facilitating repeated measurements;

FIG. 7 is a schematic illustration of a theoretical SPR Coupling Wavelength shift for a bulk gold film and a gold nanoparticles as a function of adsorbed film thickness;

FIG. 8A is a schematic illustration of yet another preferred imaging system, which incorporates a prism for full spectrum analysis;

FIG. 8B schematically illustrates data segments collected using the imaging system of FIG. 8A;

FIG. 9 schematically illustrates additional data segments collected using the imaging system of FIG. 8A;

FIG. 10A is a schematic side elevational view of an imaging system including a system of lenses in place of the prism employed in the imaging system of FIG. 9;

FIG. 10B is a schematic plan view of an imaging system including a system of lenses in place of the prism employed in the imaging system of FIG. 9;

FIG. 11 is a multi-spectral darkfield scatter analysis of ten continuous segments, 350 nm diameter beads; and FIG. 12 is a schematic illustration of yet another preferred imaging system including a prism, which is particularly well adapted to be employed for surface enhanced Raman spectroscopy detection.

DESCRIPTION OF THE PREFERRED EMBODIMENT

The present invention encompasses a method of using flow imaging systems that can combine the speed, sample handling, and cell sorting capabilities of flow cytometry with the imagery, sensitivity, and resolution of multiple forms of microscopy and full visible/near infrared spectral analysis to collect and analyze SPR spectra from objects entrained in a flow of fluid that emit an SPR spectra. Conventional methods of collecting and analyzing SPR spectra either employ a fixed sensor that emits SPR spectra as a solution of particles interacts with a fixed sensor, or emits a combined spectra from a bulk solution of particles that individually emit SPR spectra. The fixed sensor embodiment is widely used, but has a limited throughput. The spectra collected from the bulk solution does not enable spectra from individual particles to be discerned. In contrast, the present invention enables SPR spectra from individual particles to be collected with a much greater throughput than achievable using the fixed sensor prior art techniques (discussed above in connection with FIGS. 1A–1H).

Before discussing the steps employed in a preferred method in accord with the present invention, it will be beneficial to review a flow imaging system that is preferably used to execute the method. FIG. 3 illustrates the key components of an optical system employed to project light from objects in flow onto a detector (FIG. 4) that employs an exemplary readout for any particle. Objects are hydrodynamically focused into a single-file line in the fluidic system, forming a tall but narrow field of view. This approach enables the lateral dimension of the detector to be used for signal decomposition.

Referring now to FIG. 3, objects 99 are hydrodynamically focused in a flow of fluid directed into a flow cuvette 116 and illuminated from one or more sides using light sources 98 and 100. Light is collected from the objects with a high numerical aperture objective 102, and the collected light is directed along a light path including lenses 103 and slit 105. A fraction of the collected light is transmitted to an auto focus subsystem 104 and a velocity detection system 106. It should be noted that velocity detection system 106 is important to ensure the data acquired by the detection system, which are integrated over to time, increase the signal and are properly synchronized to the flow of fluid through the imaging system. In the context of the present invention, the objects are nanoparticles and micro particles including gold/ and or silver film to enable SPR spectra to be collected. It should be understood that the imaging system can be used to image a wide variety of object types, including but not limited to biological cells and beads.

The majority of the light is passed to a spectral decomposition element 108. The decomposition element employs a fan-configuration of dichroic mirrors 110 to direct different spectral bands laterally onto different regions of a TDI detector 114. Thus, the imaging system is able to decompose the image of a single object 118 into multiple sub-images 120 across detector 114, each sub-image corresponding to a different spectral component. In this view, detector 114 has been enlarged and is shown separately to highlight its elements.

Spectral decomposition greatly facilitates the location, identification, and quantification of different fluorescence-labeled bio-molecules within a cell by isolating probe signals from each other, and from background auto-fluorescence. Spectral decomposition also enables simultaneous multimode imaging (brightfield, darkfield, etc.) using band-limited light in channels separate from those used for fluorescence. FIG. 3 illustrates a typical flow-based embodiment of a flow imaging system. However, inset 101 in this Figure illustrates a plate-based embodiment of an imaging system that can be used in place of the flow-based embodiment.

Alternatively, the flow imaging system can employ a prism (as shown in FIG. 8A) or a grating oriented to disperse light laterally with regard to the axis of flow prior to the final focusing optics, for spectral analysis of each object's intrinsic fluorescence. In yet another embodiment of a suitable flow imaging system, a cylindrical final focusing lens (see FIG. 10A) can be employed to image a Fourier plane on the detector in the cross-flow axis, enabling analysis of the light scatter angle. These techniques for multi-spectral imaging, flow spectroscopy, and Fourier plane scatter angle analysis can be employed simultaneously by splitting the collected light into separate collection paths, with appropriate optics in each light path. For enhanced morphology or to analyze forward scatter light, a second imaging objective and collection train can be used to image the particles through an orthogonal facet of the flow cuvette 116, thereby viewing the objects in stereoscopic perspective with no loss of speed or sensitivity.

Turning now to FIG. 4, detector 114 of the flow imaging system shown in FIG. 3 uses a TDI that performs high throughput imaging with high sensitivity. As shown in an exemplary readout 138, the image on the TDI detector is read out one row of pixels at a time from the bottom of the detector. After each row is read out, the signals in the remaining detector pixels are shifted down by one row. The readout/shift process repeats continuously, causing latent image 142 to translate down the detector during readout (note the movement of latent image 142 through frames T1–T6). If the readout rate of the detector is matched to the velocity of the object being imaged, the image does not blur as it moves down the TDI detector. In effect, the TDI detector electronically "pans" to track the motion of an object being imaged. The key to this technique is to accurately measure the velocity of the objects being imaged and to employ that measurement in feedback control of the TDI readout rate. Thus, accurate velocity detection for objects moving in flow enables the TDI imaging to be implemented properly.

One primary advantage of TDI detection over other approaches is the greatly increased image integration period it provides. A preferred flow imaging system used in connection with the present invention includes a TDI detector that has 512 rows of pixels, giving rise to a commensurate 500× increase in signal integration time. This increase enables the detection of even faint fluorescent probes within cell images and intrinsic auto fluorescence of cells acquired at a high-throughput. When applied to nanoparticles in suspension in a cuvette 116, real-time triggering and isolation of certain nanoparticle receptor/ligand combinations for post capture analysis can be performed. For example, selective retrieval of proteins from a complex biological sample in real time can be monitored. By isolating the nanoparticle receptor/ligand combination, mass spectroscopy can be used for identity confirmation of the affinity retrained analyte via its unique molecular mass.

Furthermore, the use of a TDI detector increases measured signal intensities up to a thousand fold, representing over a 30 fold improvement in signal-to-noise ratio compared to other approaches in the prior art. This increased signal intensity enables individual particles to be optically addressed, providing high resolution measurement of either scattered spectral intensity of white light or scattered angular analysis of monochromatic light. The ability to optically address individual particles, without requiring a prism to be disposed immediately adjacent to a thin metal film significantly distinguishes the use of the preferred imaging system of FIG. 3 from the prior art SPR sensor of FIG. 1. The sensor component in FIG. 1 (the gold layer and the detector molecule) are fixed, whereas the method of the present invention employs a flow imaging system similar to that illustrated in FIG. 3, so that the "sensor" providing the SPR spectra is the gold or silver film deposited individually on particles imaged by the system. As noted above, this technique dramatically reduces the size of the detector surface, enabling more accurate data collection to be achieved.

A flow imaging system used in the present invention can be configured for multi-spectral imaging and can operate with six spectral channels: DAPI fluorescence (400–460 nm), Darkfield (460–500 nm), FITC fluorescence (500–560 nm), PE fluorescence (560–595 nm), Brightfield (595–650 nm), and Deep Red (650–700 nm). The TDI detector can provide 10 bit digital resolution per pixel. The numeric aperture of the imaging system used with this invention is typically 0.75, with a pixel size of approximately 0.5 microns. However, those skilled in the art will recognize that this flow imaging system is neither limited to six spectral channels nor limited to either the stated aperture size or pixel size and resolution.

The SPR biomolecular interaction method of the present invention, which uses an imaging system (or a substantially similar imaging system), as described above, to image nanoparticles and larger particles having a metal film will now be described in detail. The method of the present invention benefits from the ability of this preferred flow imaging system to optically address and measure individual SPR spectra of nanoparticles and larger sized particles in flow, resulting in up to a thousand-fold increase in signal collection over conventional SPR instrument designs. The steps involved in this method are schematically illustrated in FIGS. 5A–5H, and these same steps are shown as a flow chart in FIG. 6. Note that the flow chart of FIG. 6 includes an optional step that enables a user to repeat measurements, if so desired.

Referring now to FIG. 5A, in one embodiment of the method of the present invention, a solution 162 of gold coated nanoparticles 168 is introduced into a container 164. The gold coated nanoparticles have been functionalized with a "detecting" or receptor molecule attached to the surface of the gold nanoparticles. Instead of nanoparticles, gold island microbead films can be employed. Gold is preferred, but silver coated microbeads and nanoparticles are also known to enable SPR spectra to be generated and can instead be used with this invention. Combinations of gold and silver films can also be employed. Initially, container 164 has a minimal amount of a buffer solution, so as to minimize the dilution of solution 162. Preferably, any buffer solution added to container 164 should be chemically consistent with solution 162 (i.e., if solution 162 is a saline solution, any additional buffer should be a saline solution) to minimize bulk refractive index effects. It should be noted that container 164, which includes solution 162 (with functionalized gold nanoparticles, or larger particles including receptors molecules), generally corresponds to flow cell 22 in FIG. 1E. Flow cell 22 in FIG. 1E includes a functionalized gold sensor, but no analytes. Significantly, container 164 includes a plurality of individual particles, each particle acting as an individual sensor, while flow cell 22 of FIG. 1E includes only a single sensor.

Those skilled in the art will recognize that container 164 may be of any type and size capable of holding the solution, including but not limited to a beaker or test tube. Furthermore, it should be understood that FIGS. 5A–5H are not drawn to scale. For example, the amount of solution shown in the vial and its size may vary.

In a second step, schematically illustrated by FIG. 5B, an analyte solution 170 (i.e., a solution including a concentration of analyte or ligand molecules that will associate with the detection molecules bound to the individual particles in solution 162) contained in a second container 173 is added to solution 162 in container 164. While solution 170 is shown as being added as drops dispensed by a dropper, it should be understood that the present invention in not limited to that specific implementation for transferring solution 170 to container 164. For example, solution 170 may be transferred into container 164 simply by pouring it, or by a more controllable technique, such as by utilizing a micro pipette to transfer the solution. Solutions 162 and 170 combine in container 164 to form a sample solution 180, which includes gold covered nanoparticles, analyte molecules, and detector molecules bound to the nanoparticles.

In a third step schematically illustrated by FIG. 5C, about one-half of sample solution 180 is removed from container 164 via a pipette 181 or other suitable transferring technique. The removed solution 180 is introduced into a flow imaging system, such as the imaging system discussed in detail above with respect to FIG. 3. Preferably, the removed portion of solution 180 is introduced into a rotating syringe suspension pump (not separately shown). Such a pump serves to keep the particles in suspension via rotation, as well as enabling a precisely metering amount of sample to be introduced into the flow imaging system (i.e., into cuvette 116 as shown in FIG. 3). As indicated above, a preferred imaging system requires small volume injection and very precise injection rates in order to maintain synchronization between the particulate flow rate and the TDI detector read out rate. Thus, a preferred syringe pump not only rotates the sample to maintain the particles in suspension, but also provides constant volume pumping with low pulsatility. Maintaining particles in suspension enables optimal free solution conditions for association and dissociation of bio-molecular species (i.e., the analyte molecules in solution 170) to the receptors/detector molecules on the gold nanoparticles in solution 162. Achieving such free solution conditions is a major advantage over prior art planar embodiments (i.e., as shown FIGS. 1A–1H and discussed above), which are severely mass transport limited by diffusion, to time scales on the order of 16 to 160 minutes for analytes at bulk concentrations less than $10^{-7}$ M.

In addition, the flow imaging system preferably employed uses hydrodynamic focusing (i.e., uses a sheath fluid) to confine a sample fluid (solution 180) to the central portion of a cuvette 116, as indicated in FIG. 3. The sheath flow improves the precision with which the sample solution can be positioned in an observation region, enabling particles entrained in the flow of sample fluid to be more precisely imaged.

As a result of employing the flow imaging system described above to practice the method of the present invention, the absorption and/or reflected spectra of individual nanoparticles is readily measured using the TDI detector technology described in connection with FIG. 4. A peak absorbance wavelength is determined using any one of the many known "minimum hunt" algorithms to maximize precision, such as center of mass, parabolic curve fitting, and auto correlation. FIG. 5D schematically illustrates an output of this data processing, in which SPR coupling wavelength 186 is plotted as a function of time 188, during the association time period (typically between 10 and 20 minutes). Because the method of the present invention uses the flow imaging system's capability for the collection of full spectral SPR data, the entire angular or wavelength spectrum is measured, which provides a very precise measurement of the coupling angle or wavelength. This benefit is a clear advantage over the prior art, where only a single angle or single wavelength intensity can be measured. Additionally, throughput rates for imaging of macroscopic objects using this preferred imaging system are approximately 100 objects per second. When such a flow imaging system is operated in either spectral or angular dispersion mode for nanoparticles (scattered light or fluoresced light), these rates can be increased to achieve imaging of over a thousand particles per second. Also, if only one type of receptor (i.e., detection molecule, such as molecules 16 in FIG. 1A) is bound to the population of nanoparticles, then the result will be a single association kinetic binding curve. However, if many different nanoparticles (or larger sized particles supporting SPR measurements) have different types of receptor molecules, this method enables the determination of multiple kinetic association rates.

The ability to measure a library of receptor beads requires a system to identify the bead. This identification can be done in one of the following two ways. First, a library set of nanoparticles having different SPR absorption spectra can be created. This step can be carried out by using alloy nanoparticles composed of silver and gold. By adjusting the mole fractions of the alloy, up to a 150 nm separation can be achieved. Given that the kinetic association and dissociation rates are continuous, this approach enables the encoding of nanoparticles that have relatively close absorbance spectra separation (e.g., about 5 nm), so that a library of 30 beads can readily be created. Secondly, by providing gold or silver island film deposition on micron beads, bead on bead labeling can be used to encode a bead library numbering in the millions, using multiple fluorescent channel imagery. In addition, the SPR spectrum can be measured in the angular domain by using spatial light scattering. Note, spectral data and darkfield image 190 shown in FIG. 5D is exemplary of images collected from fluorescent data, and while image 190 does not illustrate SPR reflection spectra, similar images based on SPR data can be obtained using this preferred flow imaging system.

It should also be understood that by using either nanoparticles or larger microbeads as SPR sensor surfaces, the sensor area can be significantly reduced, which as noted above, is advantageous over prior art SPR sensors having larger surface areas, since a large sensor area limits the analyte sensitivity, because the SPR signal is proportional to the density of binding. Specifically, if 2 micron polystyrene beads are used with an SPR supporting gold island film, a total of 180,000 beads would allow a bead library of 100 different receptor beads, and a sub-population of 1,800 beads per receptor. This preferred flow imaging system enables one bead to be read per second over a 30 minute association/dissociation observation period. These 180,000 beads would have a cumulative sensor surface area of 0.57 square millimeters. Furthermore, if instead of island coated microbeads, 100 nanometer nano-spheres were used, the accumulative surface area would be $1.4 \times 10^{-3}$ square millimeters.

Referring now to FIG. 5E, the portion of solution 180 that remains in container 164 (the portion that was not introduced into the flow imaging system) is used to measure the dissociation rate kinetics. During the association time period (10–20 minutes—the time period corresponding to portion B of FIG. 1D), solution 180 remaining in container 164 also undergoes the same association kinetics as occurred in the portion of solution 180 that was introduced into the flow imaging system. Therefore, this bead population may be used to study the dissociation rate kinetics. To study disassociation rates, solution 180 remaining in the container is concentrated into a small portion, by centrifuging. The supernatant (i.e., the portion of the solution containing little or no particles) is removed to achieve a concentrated solution 180a of gold nanoparticles. A buffer solution 194 is added to the concentrated solution in container 164, to achieve a solution 195 that is a mixture of buffer solution 194 and concentrated solution 180a.

Immediately after buffer solution 194 is added to container 164, solution 195 is removed from container 164 and introduced into the flow imaging system discussed in detail above, as schematically illustrated in FIG. 5F. As noted above, solution 195 is preferably introduced into the flow imaging system using a rotating syringe pump.

Again, the flow imaging system generates absorption and/or reflected spectra data for each individual nanoparticles 168 in solution 195, generating spectral data as shown in FIG. 5G. The peak absorbance wavelength is determined and plotted as a function of time during the dissociation time period (typically between 5 and 15 minutes). A further optional step (not shown in FIG. 5) is necessary if the user wants to repeat the measurement. The user may utilize a low pH wash step in order to remove the bound ligands (i.e., the analytes) from the receptors attached to the gold nanoparticles, so that the nanoparticles can be used again.

FIG. 6 is a flow chart of the method schematically illustrated in FIGS. 5A–5G. The method begins in a block 200 where a container is filled with functionalized gold or silver particles. A functionalized particle is a particle in which a receptor or detector molecule (such as an antibody) is attached to a metal layer on the particle, thereby enabling SPR spectra to be generated. In a particularly preferred method, the particles are gold-plated nanoparticles. However, it should be understood that silver-coated nanoparticles, or nanoparticles coated with mixtures of gold and silver, can alternatively be employed. Further, larger sized particles supporting metal island films (also capable of generating SPR spectra) can also be alternatively employed.

Next, an analyte to be studied is added to the functionalized gold nanoparticle solution in a block 202. Half of the sample is aspirated by the preferred flow imaging system's rotational suspension pump for kinetic association analysis in a block 204. It should be understood that either more or less than half of the solution can be used in this step; using about half of the solution ensures that some solution is left to study dissociation kinetics, as described above. Further, if desired, all of the solution can be used to study association kinetics, if no data are desired from disassociation kinetics measurements.

In a block 206, the preferred flow imaging system performs continuous spectral analysis of individual particles. It should be understood that modifications can be made to the preferred imaging system described in FIG. 3, so long as the desired SPR spectral data are obtained by the resulting flow imaging system. Thus, it will be clear that the flow imaging system of FIG. 3 is merely exemplary of a system that is suitable and capable of obtaining the desired spectral data, but is not intended to be limiting of this invention.

In a block 208, the maximum absorbance wavelength versus time is plotted. While such a plot is useful, it should be understood that the method does not require the data be thus processed immediately. Instead, the raw data can be collected for review and processing at a later time.

In a block 210, the sample solution remaining in the container to which the analyte was added is concentrated, and an additional buffer solution is added (as discussed in relation to FIGS. 1D and 1F, the additional buffer is required to induce the disassociation because equilibrium drives the analytes attached to the receptor molecules bound to the nanoparticles and metal films into the buffer solution).

In a block 212, the remaining concentrated sample and the buffer solution (see FIGS. 5E and 5F) is introduced into the preferred flow imaging system for kinetic disassociation analysis. The preferred flow imaging system performs continuous spectral analysis of individual particles in a block 214. Then, once again, the maximum absorbance wavelength versus time is optionally plotted in a block 216.

A decision block 218 determines if the functionalized gold nanoparticles will be reused for further analysis of additional analytes. If so, the gold nanoparticles that have been analyzed by the flow imaging system are collected and rinsed with acid in a block 220 to remove any analyte molecules that remain bound to receptor molecules on the nanoparticles (see FIG. 1D, portion D, and FIG. 1H). If no additional analysis is required, the method is done.

FIG. 7 graphically illustrates the SPR coupling wavelength shift 230 as a function of the adsorbed film thickness 232 for a bulk gold film 234 (solid line) and nanoparticle 236 (dashed line) configurations, respectively, showing that the sensitivity of the two SPR configurations are within a factor of two of one another. Nanoparticle response curve 236 exhibits a non-linear response 240, since it represents the entire dynamic range of film thickness, and the non-linearity is due to the exponential decay of the electric field. In contrast, the bulk SPR sensor generates a substantially linear response. However, this nanoparticle response curve should not be considered as limiting the present invention.

While a linear response is generally preferred, the non-linearity and abbreviated dynamic range of nanoparticles response curve 236 should not be understood to mean that nanoparticle SPR spectra are not useful. Larger nanoparticles may be employed to increase the linearity of the curve, and calibration corrections can be made for the non-linear response. Significantly, most SPR sensorgrams do not utilize more than 40 nm in their response, but, as long as a generally linear response in that range is achieved, such spectra are useful.

The calculations employed to generate the response curves of FIG. 7 assume a bulk solution refractive index of 1.3336 (for water) and an adsorbed film refractive index of 1.45 (for proteins). The data calculated for bulk gold film assume a prism material of BK-7, incident angle of 82 degrees, and a gold film thickness of 550 Ångstroms and were calculated with a software program using a matrix form of the Fresnel reflection coefficients. The data calculated for nanoparticle assume an enhanced nanoshell (exhibiting six-times enhanced signal shift) and employ an approximation of the SPR coupling wavelength dependence described by Eq (2.0), as follows:

$$\Delta\lambda_{spr} \approx a\left[n_2^2\left(1 - \frac{1-(n_1/n_2)}{(1+(d/r_o))^3}\right)^2 - n_1^2\right] \quad (2.0)$$

Turning now to FIGS. 8A–12, various additional embodiments of a flow imaging systems that can be used for the biomolecular interaction analysis of the present invention will be discussed. FIG. 8A schematically illustrates how the preferred flow imaging system discussed in connection with FIG. 3 can be modified to be used for white light spectral scatter analysis using prism dispersion. Such a modification enables detailed spectral characterization of both gold nanoparticles and nanoparticle coated microbeads. By replacing spectral decomposition filter stack element 108, shown in FIG. 3, with a prism 290 or grating oriented to disperse laterally as shown in FIG. 8A, high resolution white light spectral scatter spectra of the nano or micro particle under analysis can be obtained. Exemplary data obtained from the imaging system of FIG. 8A are shown in FIG. 9.

FIG. 8B illustrates continously segmented data 292 from eighteen 1 micron diameter fluorescently labelled particles. The range of wavelength detection is from 488 nm to 750 nm. Each particle is imaged in the darkfield at the 488 nm excitation wavelength, and additionally, the fluorescent spectral emision from each particle is determined. The bead set analyzed contained three separate populations with different fluorescent emission spectra, as illustrated by the top three data segments 296 of the data buffer. Data segment 298 (the 6$^{th}$ segment from the top) and data segment 300 (the 16$^{th}$ segment form the top) indicate the prescence of two clumped beads. Data segment 302 (the 11$^{th}$ segment) in the fluorescent spectrum indicates the presence of three clumped beads. Thus, the preferred flow imaging system of FIG. 3 can be readily modified as indicated in FIG. 8A to achieve a tool for individually measuring the SPR spectra of nanoparticles.

FIG. 9 schematically illustrates exemplary data collected from the preferred imaging system of FIG. 3, modified as indicated in FIG. 8A, where the resulting flow imaging system enables simultaneous imaging of absorbed, scattered, and fluorescent light from objects in flow. While this configuration cannot image objects as small as nanoparticles (as opposed to collecting spectral data from such small particles), the configuration of the imaging system in FIG. 8A does allow image data from microbeads to be analyzed. As indicated above, metal island films exhibiting the SPR phenomena can be supported on micron-sized beads. Thus, the imaging system shown in FIG. 8A can be used to decode bead-on-bead libraries of metal island micron-sized beads.

FIG. 9 shows exemplary data 268 from a multispectral image data set of fluorescent calibration beads generated by the flow imaging system of FIG. 8A. Images of each bead 260 appear in a brightfield channel 262 and a darkfield channel 264, along with fluorescence images in a channel 266 in the channel corresponding to the dye present on each of the fluorescent calibration beads. This imagery was gathered at a magnification of 20×, corresponding to a pixel size of approximately 0.65 microns at the object. The darkfield 264 imagery shows the lensing effect of each bead 260 due to its large index of refraction relative to the buffer solution. A scatter plot 270 in FIG. 9 shows the discrimination power and sensitivity of the system. Though the TDI detector is linear in its response, high dynamic range is achieved, because each image covers more than 50 pixels, each of which is digitized with 8-bit resolution. With typical cell samples and the 10-bit per pixel resolution of the TDI detector, over four decades of dynamic range is achievable.

FIG. 10A is a side view, and FIG. 10B is a plan view, showing how the imaging system of FIG. 8A can be modified to enable scattered light angular analysis of the biomolecular interaction analysis using nanoparticle SPR substrates described in connection with FIGS. 5A–5H and FIG. 6. These modifications enable the detailed monochromatic angular scattered light intensity characteristic of both gold nanoparticles and nanoparticle coated microbeads. By removing dispersing prism 290 shown in FIG. 8A and replacing the focusing spherical lens 303 with a cylindrical lens 304 (FIGS. 10A and 10B), the high resolution scattered angular spatial intensity of the nano or micro particle under monochromatic side illumination can be measured.

Specifically, monochromatic light 306 from a laser source 98 (FIG. 8A) is used to illuminate a center 308 of cuvette 116. As a nanoparticle 99 enters the field of view, the laser light is scattered along light paths 310, and the scattered light is collected and collimated by a sperical collection lens 312 to achieve collimated light 314. The collimated light is then focused by a cylindrical lens 304 upon TDI detector 114. The readout rate of the TDI detector is synchronized with the flow speed of nanoparticle 99, enabling up to a thousand fold increase in signal intensity. The scattered angle spatial intensity distribution is measured along the pixelated row of TDI detector 114 (implemented as a charge coupled device (CCD) camera). For a numerical aperture of 0.75 (in air) for the collection lens, this arrangement enables the detection in a solid angle of 35 degrees, at which the SPR resonance spectra are to be observed.

FIG. 11 illustrates exemplary data collected from a early version of the flow imaging system of FIG. 3, indicating how multispectral darkfield scattering can be used to analyze particles. For particles equal in size or smaller than the pixel size in the image plane, the size of such particles can be determined by measuring the relative light scattering intensity across multiple wavelengths. The ratio of the scattered light intensities at given wavelengths is a function of the size of the particle based upon Raleigh scattering. FIG. 11 illustrates continuously segmented data from ten unlabelled beads 350, each about 350 nm in diameter. The orthogonal scattered light images were collected using 488, 532, 670, and 780 nm laser excitation. Imagery in channel 352 was collected using a 455 nm laser excitation wavelength; imagery in channel 354 was collected using a 532 nm laser excitation wavelength; imagery in channel 356 was collected using a 760 nm laser excitation wavelength; and imagery in channel 358 was collected using a 780 nm laser excitation wavelength. Current implementations of the flow imaging system of FIG. 3 have been optimized for excitation wavelengths from 400–750 nm.

For nanoparticles that are small relative to the 0.25 micron pixel size of a flow imaging system, the image acts as a spatial noise filter, excluding the pixels outside the boundaries of the nanoparticles from integrated intensity calculations, thereby enhancing the signal-to-noise ratio. For example, assuming a pixel size of 0.25 µm, the measurement of absorbance intensity from a nanoparticle that spans three pixels in a fluorescence image will have approximately 100 times less background than a non-imaging system employing a 20 µm laser spot.

As discussed above, in addition to exciting and detecting SPR spectra from individual nanoparticles and nanoparticle film microbeads, nanoparticles have also been shown to enhance various other optical processes, including Raman scattering and fluorescence through the resonance conditions due to the localized SPR. FIG. 12 illustrates how the flow imaging system of FIG. 8A can be modified to enable surface enhanced Raman spectroscopy. An optional holographic notch filter 309 is used to filter out the excitation laser light signal.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for collecting surface enhanced Raman spectra of an object in flow, where the object has a metal film capable of exhibiting surface plasmon resonance (SPR), comprising the steps of:
    (a) introducing the object into a fluid;
    (b) introducing the fluid containing the object into a flow imaging system;
    (c) illuminating the object using a coherent light source;
    (d) collecting light from the object in the flow imaging system; and
    (e) selectively removing wavelengths of light corresponding to the coherent light source from the light collected from the object to achieve filtered collected light, such that the filtered collected light comprises the surface enhanced Raman spectra, but does not include light from the coherent light source, the surface enhanced Raman spectra corresponding to SPR localized with the object.

2. The method of claim 1, wherein the surface enhanced Raman spectra data comprises infrared absorbance spectral data.

3. The method of claim 1, wherein the surface enhanced Raman spectra data comprises surface enhanced fluorescence data.

4. The method of claim 1, wherein the step of selectively removing wavelengths comprises the step of utilizing a holographic notch filter.

5. A method for collecting surface enhanced Raman spectra of an object in a flow, comprising the steps of:
    (a) introducing the object into a fluid, the object having a metal film that is capable of exhibiting surface plasmon resonance (SPR);
    (b) introducing the fluid containing the object into a flow imaging system;
    (c) illuminating the object using a light source;
    (d) collecting surface enhanced Raman spectra corresponding to SPR localized with the object, such that the surface enhanced Raman spectra collected does not include wavelengths of light corresponding to the light source.

6. A method for collecting surface enhanced Raman spectra data corresponding to interactions between a first type of molecule and a second type of molecule, comprising the steps of:
    (a) providing a plurality of objects including a metal film capable of exhibiting surface plasmon resonance (SPR);
    (b) functionalizing each object in the plurality of objects by attaching at least one molecule of the first type to the object, wherein the first type of molecule is selected because said first type of molecule preferentially interacts with the second type of molecule;
    (c) introducing the objects that have been functionalized into a fluid;
    (d) introducing a plurality of molecules of the second type into the fluid, such that an association phase is initiated;
    (e) introducing the fluid containing the objects that have been functionalized and the plurality of molecules of the second type into a flow imaging instrument capable of collecting surface enhanced Raman spectra data; and
    (f) using the flow imaging instrument to collect surface enhanced Raman spectra data from individual objects passing through the flow imaging instrument, such that the collected surface enhanced Raman spectra data does not include wavelengths of light used to illuminate the individual objects.

7. The method of claim 6, wherein the step of using the flow imaging instrument comprises the steps of:
    (a) illuminating the plurality of objects using a coherent light source;
    (b) collecting light from the plurality of objects in the flow imaging system; and
    (c) selectively removing wavelengths of light corresponding to the coherent light source from the light collected from the plurality of objects, such that the collected light comprises the surface enhanced Raman spectra, and not light from the coherent light source.

8. The method of claim 7, wherein the step of selectively removing wavelengths comprises the step of utilizing a holographic notch filter.

9. The method of claim 6, wherein the step of introducing the fluid into the flow imaging instrument comprises the steps of:
    (a) determining a length of an association period for the fluid; and
    (b) introducing the fluid into the flow imaging system at a substantially constant rate for substantially the length of the association period.

10. The method of claim 6, wherein the step of introducing the fluid into a flow imaging instrument comprises the step of introducing a first portion of the fluid into the flow imaging instrument, such that a second portion of the fluid remains.

11. The method of claim 10, further comprising the steps of:
    (a) determining a length of an association period for the fluid;
    (b) after the association period has expired, adding a buffer solution to the second portion of the fluid, the buffer solution having been selected to induce disassociation of molecules of the second type that are bound to molecules of the first type;
    (c) introducing the second portion of the fluid with the buffer solution into a flow imaging instrument capable of collecting surface enhanced Raman spectra data; and
    (d) using the flow imaging instrument to collect surface enhanced Raman spectra data from individual objects in the second portion of the fluid as the objects pass through the flow imaging instrument.

12. The method of claim 11, wherein after the association period has expired, and before adding the buffer solution to the second portion, further comprising the steps of:
    (a) processing the second portion of the fluid to separate the second portion of the fluid into a concentrated solution of objects and a supernatant; and
    (b) removing the supernatant from the second portion of the fluid that was processed.

13. The method of claim 6, further comprising the steps of:
(a) collecting the objects after they have passed through the flow imaging system; and
(b) rinsing the objects that were collected in an acid rinse, to remove any molecules of the second type that remain bound to the molecules of the first type, so that the objects that were collected and rinsed can be reused.

14. A method for collecting surface enhanced Raman spectra of an object in flow, where the object has a metal film capable of exhibiting surface plasmon resonance (SPR), comprising the steps of:
(a) introducing the object into a fluid;
(b) introducing the fluid containing the object into a flow imaging system; and
(c) collecting surface enhanced Raman spectra corresponding to SPR localized with the object, wherein the surface enhanced Raman spectra comprises at least one type of data selected from the group consisting essentially of:
  (i) infrared absorbance spectral data; and
  (ii) surface enhanced fluorescence data.

15. A method for collecting surface plasmon resonance (SPR) spectra of an object in flow, where the object has a metal film capable of exhibiting SPR, comprising the steps of:
(a) introducing the object into a fluid;
(b) introducing the fluid containing the object into a flow imaging system; and
(c) collecting spectral SPR data corresponding to the object, the spectral SPR data including at least one of:
  (i) an angular spectrum corresponding to the object, where the angular spectrum includes a resonance dip associated with SPR; and
  (ii) a wavelength spectrum corresponding to the object, where the wavelength spectrum includes an absorbance dip associated with SPR.

16. A method for collecting surface plasmon resonance (SPR) spectra of an object, in a flow, comprising the steps of:
(a) introducing the object into a fluid, the object having a metal film that is capable of exhibiting SPR;
(b) introducing the fluid containing the object into a flow; and
(c) collecting spectral SPR data corresponding to the object as the object is carried in the fluid by the flow, the spectral SPR data including at least one of:
  (i) an angular spectrum corresponding to the object, where the angular spectrum includes a resonance dip associated with SPR; and
  (ii) a wavelength spectrum corresponding to the object, where the wavelength spectrum includes an absorbance dip associated with SPR.

* * * * *